(12) United States Patent
Serrahima Tornel et al.

(10) Patent No.: US 9,782,266 B2
(45) Date of Patent: Oct. 10, 2017

(54) DEVICE FOR REPAIRING AN INTERVERTEBRAL DISC

(71) Applicant: NEOS SURGERY, S.L., Cerdanyola Del Valles (ES)

(72) Inventors: Marc Serrahima Tornel, Sant Cugat Del Valles (ES); Salvador Llas Vargas, Lleida (ES); Ana Rodriguez Alonso, Abrera (ES); Montserrat Charles-Harris Ferrer, Barcelona (ES); Lluis Chico Roca, Badalona (ES); Pablo Clavel Laria, Barcelona (ES)

(73) Assignee: NEOS SURGERY, S.L., Del Valles (ES)

( * ) Notice: Subject to any disclaimer, the term of this patent is extended or adjusted under 35 U.S.C. 154(b) by 6 days.

(21) Appl. No.: 14/777,283

(22) PCT Filed: Mar. 12, 2014

(86) PCT No.: PCT/EP2014/054894
§ 371 (c)(1),
(2) Date: Sep. 15, 2015

(87) PCT Pub. No.: WO2014/140136
PCT Pub. Date: Sep. 18, 2014

(65) Prior Publication Data
US 2016/0015521 A1    Jan. 21, 2016

(30) Foreign Application Priority Data
Mar. 15, 2013 (EP) .................................. 13159635

(51) Int. Cl.
*A61F 2/44* (2006.01)
*A61F 2/30* (2006.01)

(52) U.S. Cl.
CPC .............. *A61F 2/442* (2013.01); *A61F 2/441* (2013.01); *A61F 2002/302* (2013.01);
(Continued)

(58) Field of Classification Search
CPC ...................... A61F 2/442; A61F 2/441; A61F 2002/30092; A61F 2002/302;
(Continued)

(56) References Cited

U.S. PATENT DOCUMENTS

2004/0039392 A1* 2/2004 Trieu ...................... A61F 2/442
606/86 R
2004/0210310 A1* 10/2004 Trieu ...................... A61F 2/442
623/17.11

(Continued)

FOREIGN PATENT DOCUMENTS

WO      0234169 A2    5/2002
WO   2006060482 A2    6/2006

(Continued)

OTHER PUBLICATIONS

Written Opinion and International Search Report in corresponding International Application No. PCT/EP2014/054894, mailed on Jul. 8, 2014.
(Continued)

*Primary Examiner* — Pedro Philogene
*Assistant Examiner* — David C Comstock
(74) *Attorney, Agent, or Firm* — Edell, Shapiro & Finnan LLC

(57) ABSTRACT

A device (1, 100) for repairing an intervertebral disc comprising an anchoring body (2, 102), suitable for being advanced into and secured in one of the vertebrae adjacent the intervertebral disc; and a prosthesis (3, 103, 203, 303) attachable in a secure coupling position to the anchoring body (2, 102) and adapted for retaining or replacing the
(Continued)

nucleus pulposus in an interior space of an outer annulus of the intervertebral disc, the anchoring body supporting and arranging in the cited coupling position the prosthesis such that the prosthesis is oriented to in a direction toward and through a hole in the outer annulus, the prosthesis comprising at least one active portion (4) adapted to assume and maintain a first placement shape (A) suitable for permitting the active portion to be inserted into and through the hole in the outer annulus during a placement thereof into the interior space of the outer annulus, and at least a second operative shape (B) suitable for at least partially occluding the hole in the outer annulus and/or replacing at least a portion of the nucleus pulposus upon the active portion assuming a placement position in the interior space of the outer annulus.

32 Claims, 10 Drawing Sheets

(52) U.S. Cl.
CPC ............... *A61F 2002/30092* (2013.01); *A61F 2002/30387* (2013.01); *A61F 2002/30433* (2013.01); *A61F 2002/30581* (2013.01); *A61F 2002/444* (2013.01); *A61F 2002/4415* (2013.01); *A61F 2002/4435* (2013.01); *A61F 2220/0016* (2013.01)

(58) Field of Classification Search
CPC .. A61F 2002/30387; A61F 2002/30433; A61F 2002/30581; A61F 2002/4415; A61F 2002/4435; A61F 2002/444; A61F 2002/0016
USPC ...................................................... 623/17.16
See application file for complete search history.

(56) References Cited

U.S. PATENT DOCUMENTS

| | | |
|---|---|---|
| 2005/0015151 A1* | 1/2005 | Fortin .................. A61F 2/442 623/17.13 |
| 2005/0234557 A1 | 10/2005 | Lambrecht et al. |
| 2006/0064171 A1* | 3/2006 | Trieu ..................... A61F 2/441 623/17.16 |
| 2006/0089646 A1* | 4/2006 | Bonutti ............. A61B 17/0218 606/279 |
| 2006/0217747 A1 | 9/2006 | Ferree |
| 2006/0247784 A1* | 11/2006 | Kim .................... A61F 2/442 623/17.16 |
| 2006/0287727 A1* | 12/2006 | Segal .................. A61F 2/441 623/17.12 |
| 2006/0293753 A1 | 12/2006 | Thramann |
| 2007/0162132 A1 | 7/2007 | Messerli |
| 2007/0185497 A1* | 8/2007 | Cauthen ............ A61B 17/0057 606/99 |
| 2008/0009878 A1* | 1/2008 | McLeod ................ A61F 2/442 606/86 R |
| 2010/0094425 A1 | 4/2010 | Bentley et al. |
| 2010/0114317 A1 | 5/2010 | Lambrecht et al. |
| 2011/0295276 A1* | 12/2011 | Wales ................ A61B 17/0401 606/139 |
| 2012/0316648 A1 | 12/2012 | Lambrecht et al. |

FOREIGN PATENT DOCUMENTS

| WO | 2007084427 A2 | 7/2007 |
|---|---|---|
| WO | 2008094217 A1 | 8/2008 |

OTHER PUBLICATIONS

Intention to Grant in corresponding European Patent Application No. 14709664.8, mailed on Sep. 12, 2016.

* cited by examiner

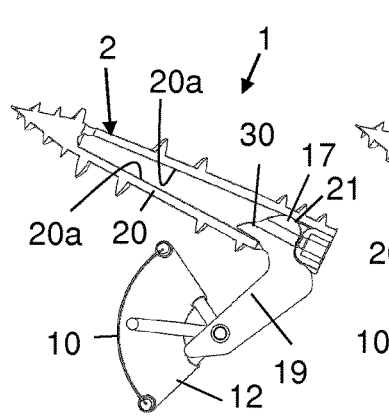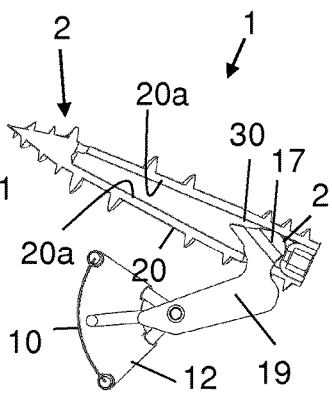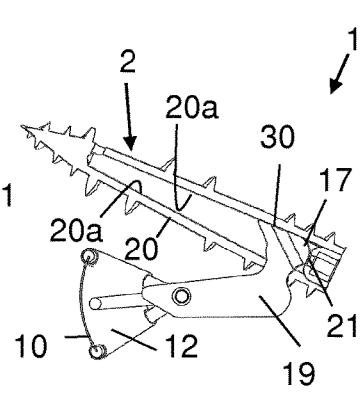
Fig. 6a   Fig. 6b   Fig. 6c
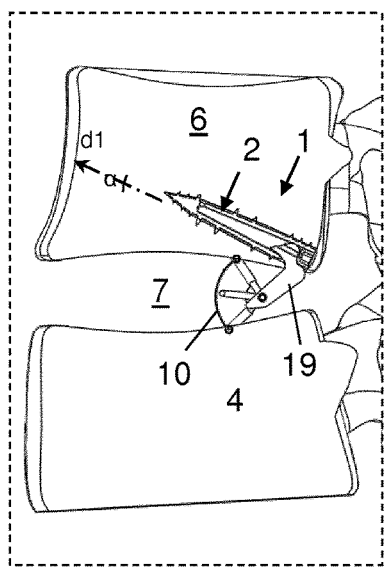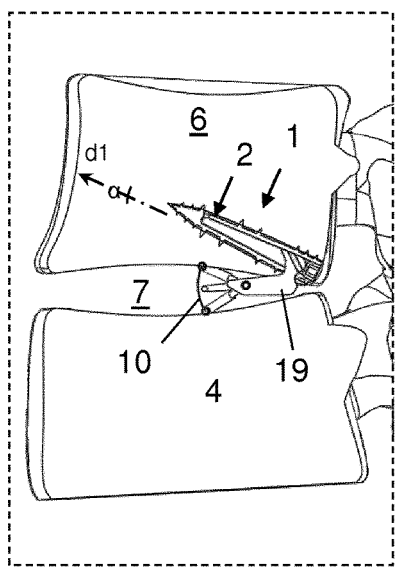
Fig. 7a   Fig. 7b

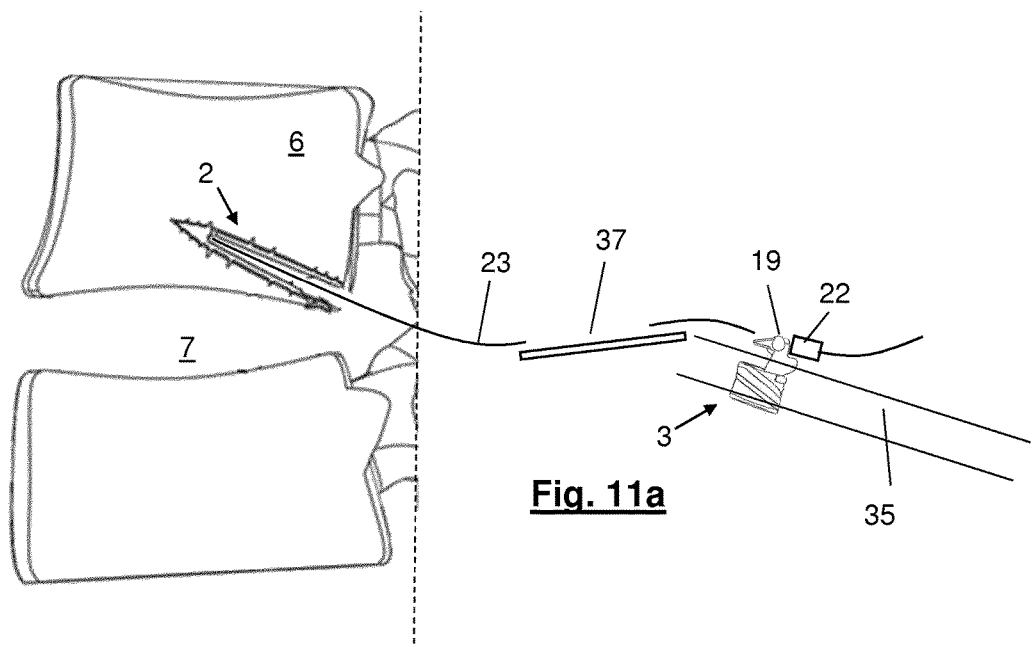
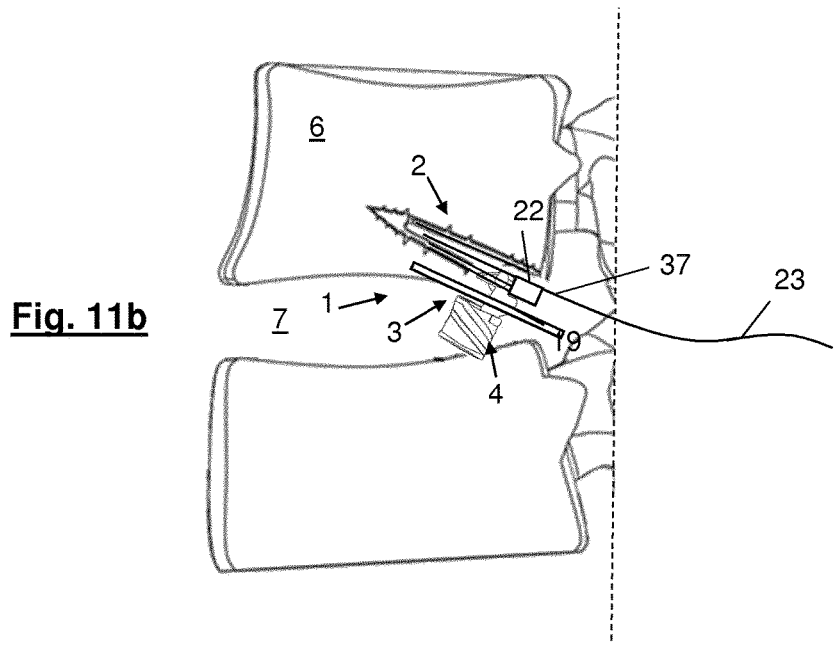

DEVICE FOR REPAIRING AN INTERVERTEBRAL DISC

TECHNICAL FIELD

The invention disclosed herein relate to osteoimplantable devices for use in repairing intervertebral discs.

BACKGROUND OF THE INVENTION

When the intervertebral disc arranged between two vertebrae is damaged, the nucleus pulposus which the disc encloses in its interior can seep out of the disc through the damaged zone causing a disc herniation. This hernia often results in pain as a result of the hernia contacting nerves in the surrounding area. Damage to surrounding nerves may also occur. For this reason it is necessary to remove the hernia and repair the damaged zone of the disc in order to retain the nucleus within the disc and thus prevent re-herniation.

Devices for retaining the leakage of the nucleus pulposus caused by the rupture of the intervertebral disc are known. For example, U.S. Publication No. US2008/0082168 discloses a device that consists of a band to be applied against the rupture of the vertebral disc which is fixed in position by means of a plurality of strips forming loops that go through respective perforations made in the vertebrae immediately above and below the disc to be repaired. This means that the perforations have to be made prior to the insertion of the device, which complicates the process of implanting the device. In addition to being difficult to implant, the devices require the surgeon to be skilful not only in passing the strips through the perforations, but also in subsequently tying them and all this without the band losing tension.

International Publication WO2010/40107 discloses a system for repairing a herniated intervertebral disc by means of applying a patch-like mesh which covers the herniated disc. The mesh is anchored to the vertebrae immediately above and below the disc to be repaired by means of elements in the form of a hook or fasteners. The mesh is capable of being folded for the introduction thereof in the repair zone and subsequently anchored. The system requires first having the mesh and then correctly maintaining its position while the hooks or fasteners are secured, making the correct fixing thereof difficult.

Devices for repairing a damaged zone in an intervertebral disc by means of sutures are also known, For example, International Publication WO2006/119034 discloses a device formed by a suture thread and a set of anchors for its fastening in the intervertebral disc. The device allows suturing the damaged zone of the intervertebral disc by means of introducing an expandable support inside the disc in which the anchors of the thread are tacked through the disc. These anchors allow securing the suture to the disc and thus being able to close the damaged zone. If the damaged zone of the disc is close to its upper or lower end, the device can further incorporate a point for anchoring the suture in the vertebra adjacent to the damaged zone, as shown in the alternative variant described in International Publication WO2010/045179. A problem associated with such devices that are formed by suture is that they are not very rigid and are therefore difficult to be correctly inserted. Furthermore, the suture can weaken over time, even break, as the zone of the disc to which it is secured gives, for example if the damaged zone of the disc becomes larger.

International Publication WO02058599 discloses another type of osteoimplantable device that consists of an expandable plug acting as a stopper filling the damaged zone of the disc and anchoring means for anchoring the stopper which allows fixing the stopper to the vertebrae adjacent to the plugged disc, preventing the plug from moving. To implant such devices it is necessary for the opening made in the patient's body to be the size of the intervertebral space in order to introduce it. As a result, such devices cannot be implanted in a minimally invasive manner. Such devices also require the surgeon to fix the device to the vertebra after having introduced the plug in the damaged zone of the disc, making it difficult to keep the plug in the correct position during the fixing operation.

A first objective of the resent invention is to disclose an alternative to known osteoimplantable devices for use in repairing an intervertebral disc.

Another objective of the present invention is to disclose an osteoimplantable device for repairing a rupture of an intervertebral disc that is compact and requires minimally invasive surgery.

It is also desirable for the device to not protrude from the vertebra towards the space occupied by the nerve.

Another objective of the present invention is to also disclose an osteoimplantable device for repairing a rupture of an intervertebral disc which allows being adapted to the variations that the intervertebral space may experience, for example due to the reduction of the intervertebral space as a result of degenerative changes, such as spondylitis.

DISCLOSURE OF THE INVENTION

The device of the invention comprises an anchoring body, suitable for being advanced into and secured in one of the vertebrae adjacent the intervertebral disc; and a prosthesis attachable in a coupling position to the anchoring body and adapted for retaining or replacing the nucleus pulposus in an interior space of an outer annulus of the intervertebral disc, the anchoring body supporting and arranging in the cited coupling position the prosthesis such that the prosthesis is oriented to in a direction toward and through a hole in the outer annulus, the prosthesis comprising at least one active portion adapted to assume and maintain a first placement shape suitable for permitting the active portion to be inserted into and through the hole in the outer annulus during a placement thereof into the interior space of the outer annulus, and at least a second operative shape suitable for at least partially occluding the hole in the outer annulus and/or replacing at least a portion of the nucleus pulposus upon the active portion assuming a placement position in the interior space of the outer annulus.

According to some implementations the anchoring body has an elongated shape, determining a first end and a second end, and the prosthesis extends from a side of the anchoring body in the mentioned coupling position in a manner so as not to protrude from the vertebra towards the space occupied by a nerve.

As will be described in more detail below, according to some implementations when securing the anchoring body to the vertebra, the prosthesis is already coupled to the anchoring body. According to other implementations the prosthesis is coupled to the anchoring body after the anchoring body has been secured to the vertebra. In any case, the orientation of the active portion of the prosthesis during the insertion maneuver for the insertion thereof into the intervertebral space will be conditioned or will be guided by the position adopted by the mentioned anchoring body.

According to some implementations when the device is intended for occluding a rupture in a intervertebral disc, the active portion of the prosthesis is provided with the necessary properties so that the active portion tends to adopt the operative shape by default, this active portion of the prosthesis being provided with retaining means that force it to adopt its placement shape, the retaining means being manipulable or removable in order to disable its retaining function once the active portion of the prosthesis is inserted into the intervertebral space. According to some implementations the retaining means binds the active portion of the prosthesis to keep it in its placement shape. The retaining means may comprise, for example, a thread cooperating in the fastening of the active portion of the prosthesis in its placement shape with ties or knots.

It is of interest that for occluding a rupture in the intervertebral disc, the placement shape is a compact shape and the operative shape is an expanded shape in relation to the mentioned shape.

According to some implementations the active portion of the prosthesis comprises a flexible membrane supported in a frame with elastic and shape memory properties that gives the active portion of the prosthesis the capability to automatically transition from the first compact placement shape, in which the membrane is folded, to the second expanded operative shape, in which the membrane is unfolded. According to some implementations the frame comprises a spiral-shaped filamentous element which expands to give the membrane an arch shape.

Therefore according to one variant, the frame comprises a spiral-shaped filamentous element which expands into a sort of fan from a placement position determined by the first shape and gives the membrane an arch shape.

According to another feature of the invention, the anchoring body extends longitudinally according to an anchoring vector and the active portion of the prosthesis adopts an oblong configuration in the first compact shape. In such implementations the anchoring body and the prosthesis may be prepared to be coupled to one another such that the active portion of the prosthesis is suspended from the anchoring body and oriented such that it is coplanar with the anchoring vector. According to some implementations the anchoring body and the prosthesis are prepared to be coupled to one another after the anchoring body is secured in the vertebra.

According to some implementations the anchoring body comprises a longitudinal portion in the form of a tube, preferably with outer threading, defining a mouth through which a connection portion of the prosthesis can be tightly introduced in the anchoring body, the tube being provided with at least one assembly groove so that an extension of the connection portion of the prosthesis, attached to the active portion of the mentioned prosthesis, can emerge from the anchoring body through the side wall of the tube. Alternatively, the threading of the anchoring body may be replaced with other anchoring means such as a set of teeth protruding from the anchoring body and allowing the insertion thereof under pressure into the vertebra. According to some implementations the connection portion of the prosthesis, which is housed inside the tube, is provided with a support surface which slides over the inner face of the side wall of the tube to allow a controlled play between this connection portion and the anchoring body, and thereby of the prosthesis with respect to the mentioned anchoring body. According to some implementations the device further comprises a closure part that can be inserted into the mouth of the tube.

According to some implementations at least a portion of the longitudinal portion of the anchoring body is in the form of a tube. In such implementations, first end of a thread, cable or the like is secured in the longitudinal portion of the anchoring body with the thread, cable or the like extending through an inner cavity thereof towards and out of the mouth. According to some implementations the thread, cable or the like extends a sufficient distance so as to be able to emerge from a patient during the implantation of the device. The connection portion of the prosthesis, and where appropriate the closure part, are provided with respective through holes through which the free end of the complementary thread, opposite the first end, can be inserted.

According to some implementations the anchoring body is configured in the form of a screw extending along a longitudinal axis and the prosthesis is coupled to the anchoring body with the possibility of rotation about the longitudinal axis.

According to some implementations when the prosthesis is intended for replacing all or a portion of the nucleus pulposus, the placement shape of the active portion of the prosthesis is a substantially straight shape and the operative shape is one of a toroidal, a horseshoe arch or spiral shape, the outer contour of which adapts to the space available in the cavity of a damaged human intervertebral disc. Other placement and operative shapes of the prosthesis are also contemplated.

According to some implementations the active portion of the prosthesis comprises a core made of an implantable material, such as a wire or a metal strand, with elastic and/or shape memory properties. According to some implementations the wire or metal strand is at least partially covered by one or more buffering elements.

An advantage of the type of osteoimplantable devices disclosed herein is an ability for the devices to be implanted using minimally invasive surgical procedures. The devices may also be adapted to the variations that the intervertebral space may experience, for example due to the reduction of the intervertebral space as a result of degenerative changes, such as spondylitis.

BRIEF DESCRIPTION OF THE DRAWINGS

FIGS. 6a to 6c show a sequence illustrating the behavior of the third variant of the invention when a collapse of the original intervertebral space occurs;

FIGS. 7a and 7b show the behavior of the variant of the invention according to FIGS. 6a to 6c in the implantation environment;

FIGS. 11a and 11b show a sequence illustrating the behavior of the alternative embodiments in the implantation environment;

DETAILED DESCRIPTION

Figure 1:
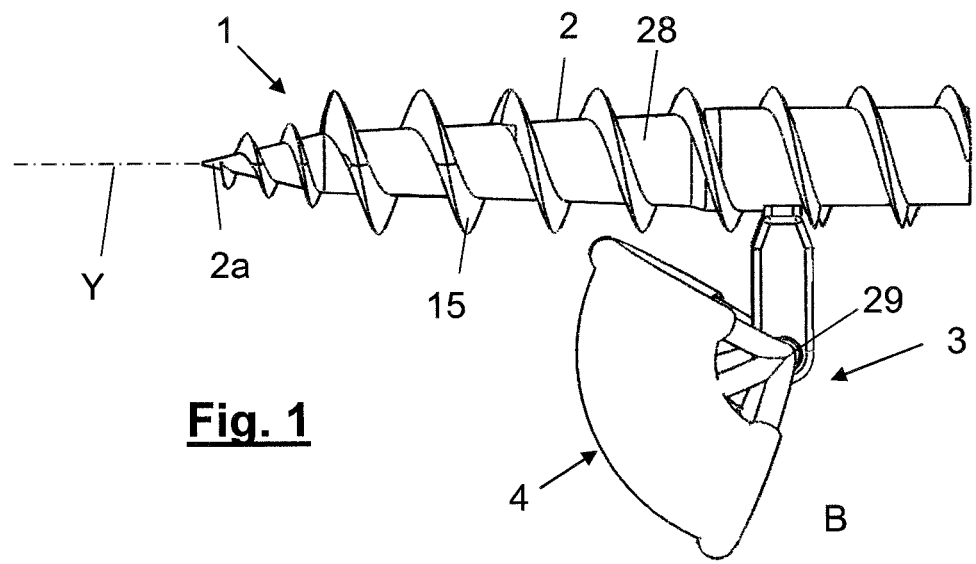
FIG. 1 is a perspective view of a device according to a first variant of the present invention.

FIG. 1 shows an implementation of an intervertebral disc repair device 1 in an operative position. The device 1 comprises an anchoring body 2, configured in the form of a headless screw 28 having a first sharp or tip-shaped end 2a and a second end 2b. A prosthesis 3 is coupled to the anchoring body 2. As illustrated in FIG. 1, the prosthesis 3 is supported such that it is suspended from a side of the anchoring body 2 and comprises an active portion 4, explained in greater detail below, which is oriented in a forward direction, i.e., in the forward movement direction of the anchoring body 2 during its implantation in the vertebra.

Figure 2:
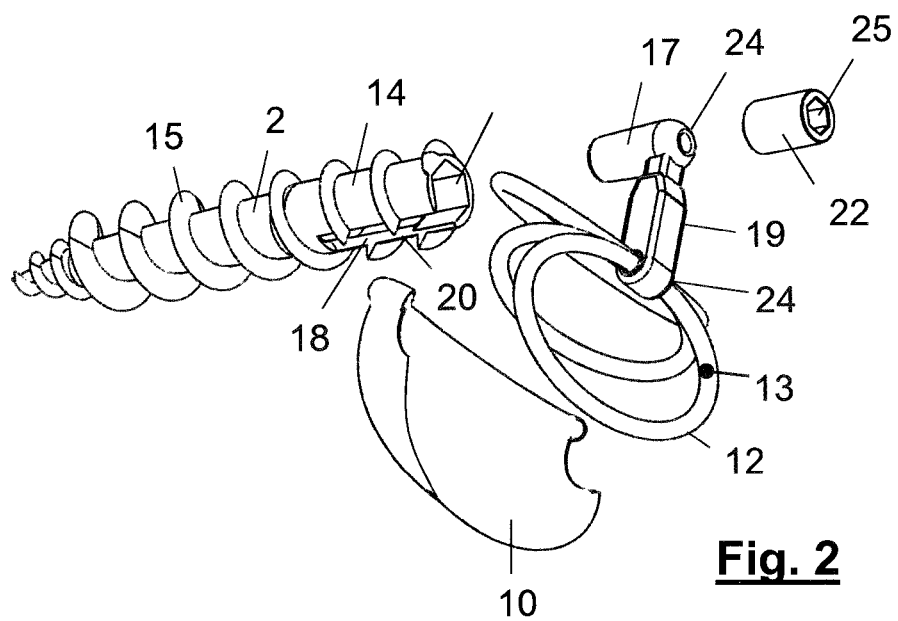
FIG. 2 is an exploded view of the device according to FIG. 1.

Since this variant is suitable to first anchor or screw the anchoring body 2 to the vertebra, the anchoring body 2 and the prosthesis 3 are prepared to be coupled to one another after the anchoring body 2 is secured in the vertebra. For this purpose, as shown in FIG. 2, the anchoring body 2 comprises a longitudinal portion in the form of a tube 14 that extends distally from a mouth 16 at the second end 2b of the anchoring body 2 through which a connection portion 17 of the prosthesis 3 can be tightly introduced therein until reaching a secure coupling position. The tube 14 is provided with an assembly groove 18 to guide an extension 19 of the connection portion 17 of the prosthesis 3 which is attached to the active portion 4 of the prosthesis 3. The extension 19 of the connection portion 17 extends through the groove 18, emerging from the anchoring body 2 through the side wall 20 of the tube 14.

Figure 4:
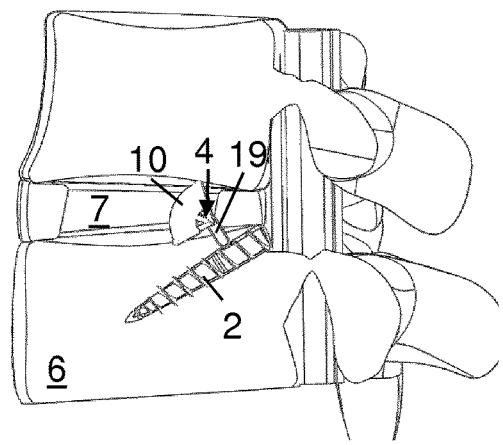
FIG. 4 shows the device according to FIGS. 1 and 2 with its components in their secure coupling position and duly implanted in a patient.

In the position depicted in FIGS. 1 and 4, the prosthesis 3 extends from one side of the anchoring body 2 so that no portion of the prosthesis 3 extends through the rear portion or second end 2b of the anchoring body 2 and therefore does not interfere with the nerve juxtaposed with the rear wall of the vertebrae.

According to some implementations, the mouth 16 of the tube 14 is adapted for receiving a tool (not shown) suitable for transmitting a specific tightening torque to the anchoring body 2. According to some implementations the anchoring body 2 is flexible along at least a portion of its length for the purpose of being able to implant the screw 28 following a trajectory that is different from the trajectory of the tip of the tool that is used for torqueing the anchor body 2.

Such implementations take advantage of the precision with which the operation of screwing the anchoring body 2 in the vertebra can be performed, in the sense that the anchoring body 2 can be arranged to follow an optimal direction with the aid of suitable means and instruments, which usually comprise taking X-rays during the operation. This precision assures the proper positioning of the prosthesis 3 during the operation of inserting the active portion 4 into the damaged portion of the disc, during which the prosthesis is guided by the tube 14 and the assembly groove 18 of the anchoring body 2. The direction for screwing in the anchoring body 2 is the direction determined by an anchoring vector d1 which forms an angle α (see, for example FIGS. 7a and 7b) with the horizontal. According to some implementations the angle α is between about 15 degrees and about 35 degrees, and preferable between about 20 degrees and about 30 degrees.

As shown in FIG. 2, the device 1 may further comprise a closure part 22 that can be inserted into the mouth 16 of the tube 14 once the prosthesis 3 is duly coupled with the anchoring body 2.

FIGS. 1 and 2 show the prosthesis 3 with its active portion 4 adopting an expanded operative shape (B). According to some implementations the device 1 is prepared so that this active portion 4 of the prosthesis 3 adopts and maintains a compact placement shape (A) with respect to the expanded operative shape during the coupling of the prosthesis 3 to the anchoring body 2 and during its insertion into the intervertebral space, advantageously allowing this insertion to be performed in the patient in a minimally invasive manner, for example through a cannula 35, and the active portion 4 of the prosthesis to be inserted into the intervertebral space through a narrow opening or an opening with a small clearance in the intervertebral disc.

According to some implementations, as shown in the examples of FIGS. 1, 2 and 4, the active portion 4 of the prosthesis 3 comprises a flexible membrane 10 supported on a frame 12, the frame 12 having elastic and/or shape memory properties that give the active portion 4 of the prosthesis 3 the capability to automatically go from the first compact placement shape (A), such as that depicted in FIG. 3, in which the membrane (not depicted in this FIG. 3) is folded, to the second expanded operative shape (B), such as that depicted in FIGS. 1, 2 and 4 in which the membrane 10 is unfolded. Since the active portion 4 of the prosthesis 3 tends to adopt the operative expanded shape (B) by default, the active portion 4 of the prosthesis 3 may be provided with retaining means 8 that force or otherwise constrains the prosthesis in its compact placement shape (A). The retaining means 8 is manipulable in order to disable the retaining function once the active portion 4 of the prosthesis is inserted into the intervertebral space, which according to some implementations occurs once the prosthesis 3 is coupled in the anchoring body 2.

In the example of FIGS. 1 to 4, the frame 12 comprises a filamentous element 13 which expands from a compressed position determined by the first compact placement shape (A), as depicted in FIG. 3. According to some implementations, when expanded, the frame 12 gives the membrane 10 an arch or curved shape as depicted in FIGS. 1, 2 and 4. Expansion can be obtained by modeling the frame 12 in an elastic material with shape memory properties, such as nitinol. In this case, it is possible to previously fix in the frame 12 an expanded shape that it will tend to adopt by means of suitable thermal treatment.

According to some implementations the frame 12 has a spiral shape comprising a plurality of coils. In the examples of FIGS. 1 through 3 the frame comprises three coils. However, the use of spiral shapes with a larger number of coils is contemplated. It is also contemplated that the frame 12 has other shapes that allow adopting a compressed position and an expanded position, such as ribs or a set of rods connected at one end and which can be extended like an umbrella.

Figure 3A:
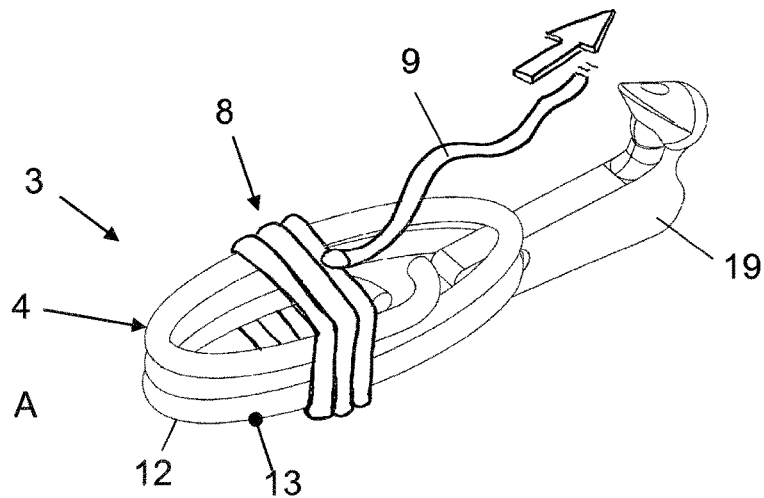
FIG. 3 illustrates an implementation by which an active portion of a prosthesis is maintained in a placement shape prior to insertion into an associated intervertebral space.

In the example of FIG. 3a the first placement shape (A) of the active portion 4 of the prosthesis 3 is elongated. The solution for coupling the anchoring body 2 and the prosthesis 3 by use of the assembly groove 18 in the side wall 20 of the anchoring body 2 facilitates the prosthesis 3 being suspended from the anchoring body 2 in a manner in which the active portion 4 is oriented such that it is coplanar with the anchoring vector (d1) of the anchoring body 2 (see, for example, FIGS. 7a and 7b). In the example shown, the anchoring vector (d1) coincides with the longitudinal axis of the screw 28.

In FIG. 3a, the retaining means 8 binds the active portion 4 of the prosthesis 3 to maintain it in its compact placement shape (A). The retaining means 8 may comprise a thread 9, such as a suture thread made of an absorbable material such as Vicryl™, cooperating in the fastening of the active portion 4 of the prosthesis 3 in its compact shape (A) with ties or knots. To effectuate an expansion of the prosthesis from its compact placement shape, the thread 9 may be cut or alternatively the ties or knots may be manipulated to remove the binding effect of thread 9 about the active portion 4 of the prosthesis 3 when the active portion 4 is correctly arranged in the intervertebral space. The use of a sleeve, cannula or similar type device may also be used to maintain the active portion 4 of the prosthesis in its compact placement shape (A).

Figure 3B:
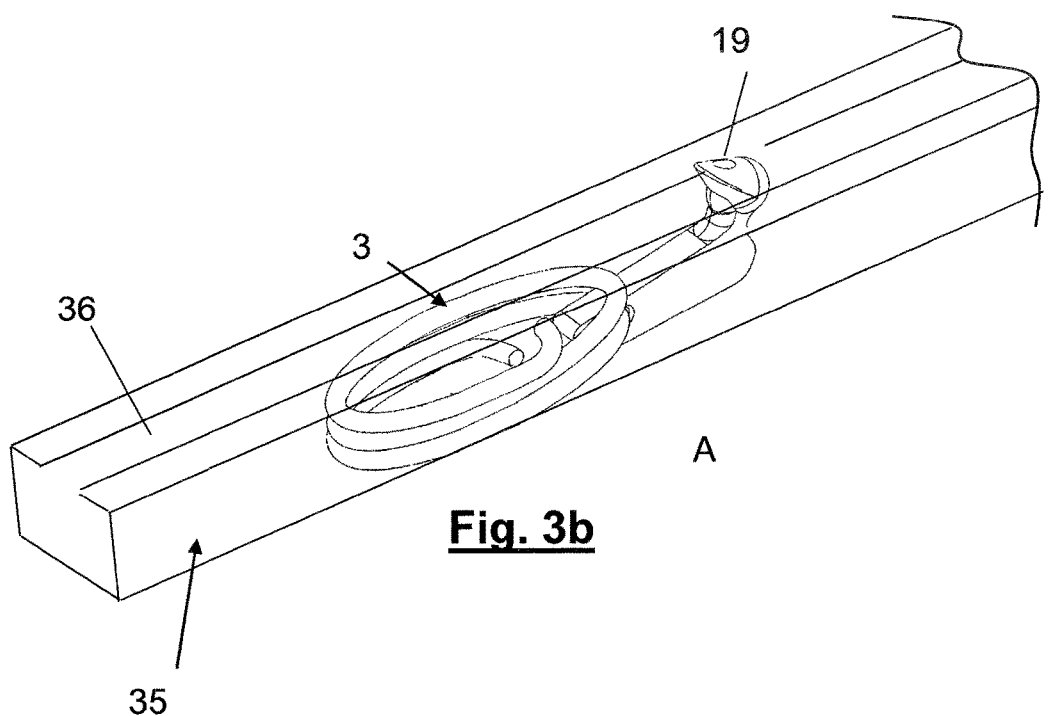

FIG. 3b shows an embodiment where the retaining means 8 in which the active portion 4 of the prosthesis 3 is housed comprises a cannula 35 to maintain the active portion 4 of the prosthesis 3 in its compact placement shape (A). The active portion 4 of the prosthesis 3 is housed in said cannula 35 and it is prepared to be expelled through an overture of said cannula 35, for example one of its ends by pushing the active part with a dedicated tool, once said end of the cannula 35 is correctly placed in the intervertebral space.

The cannula 35 can also present a longitudinal grove 36 arranged to allow the transit of the extension 19 of the connection portion 17 of the prosthesis 3, which is attached to the active portion 4 of the prosthesis 3.

The active portion 4 of the prosthesis 3 is preferably housed in the cannula 35 during its manufacturing, compressing the active portion 4 of the prosthesis 3 with specialized machinery that would allow correctly pre-charging the active portion 4 in the cannula 35. The active portion 4 of the prosthesis 3 can then advantageously be presented to the doctor in a sterilized package, already placed in the cannula and ready to be open and directly implanted to a patient without the doctor having to further manipulate the prosthesis 3 before its introduction.

According to some implementations the sleeve or cannula is capable of being removed in order to release the active portion 4 of the prosthesis 3 so that it may assume its expanded shape. According to other implementations the active portion 4 of the prosthesis is extracted from the retaining means in order to release the active portion 4 of the prosthesis 3 so that it may assume its expanded shape.

According to some implementations the frame 12 unfolds like a fan, which gives the active portion 4 of the prosthesis a shape generally similar to a parachute in its expanded state. Such a shape allows the active portion 4 of the prosthesis to adapt to the intervertebral space existing at the time of implanting the device 1. It also permits the active portion 4 adapt to the smaller intervertebral space that may result over time as a result of a collapse of the intervertebral disc.

In the example illustrated in FIGS. 1 and 2, the extension 19 joining the connection portion 17 of the prosthesis 3 with the active portion 4 is formed by a slightly bent arm forming a single part with the connection portion 17. According to some implementations the arm is finished at one end with a clamp 29, clip or similar fastening means that connects the arm to a portion of the frame 12, such as to the coils as depicted in FIG. 2. According to some implementations the arm is flexible. The arm may also be formed by a prolongation of a portion of the frame 12, such as, for example, a prolongation of one or more of the filamentous elements 13. The arm may comprise any of a variety of biocompatible materials and is preferably constructed of a metallic material.

The shape that the arm requires for arranging the active portion 4 of the prosthesis 3 in the suitable location within the intervertebral space can be an obstacle hindering the prosthesis 3 from adapting to a very small intervertebral space as the result of a significant collapse of the intervertebral disc. Implementations according to the operational characteristics of what is shown in FIGS. 6a, 6b and 6c are aimed at addressing this problem.

The sequence of FIGS. 6a to 6c shows a longitudinal section view of a variant of the device 1 in which the connection portion 17 of the prosthesis 3 is suitable to allow certain play in the coupling between the prosthesis 3 and the anchoring body 2. In practice, this variant allows the articulated attachment of the prosthesis 3 to the anchoring body 2 so that the prosthesis 3 may attain a variety of angular orientations with respect to the anchoring body 2 as shown in FIGS. 6a to 6c.

According to some implementations the connection portion 17 of the prosthesis 3 which is housed inside the tube 14 of the anchoring body 2 is provided with a support surface 21 which slides over the inner face 20a of the side wall 20 of the tube 14 to allow controlled play between the connection portion 17 and the anchoring body 2. In the example of FIGS. 6a to 6c the support surface 21 is configured in the form of a hemispherical cap and comprises a projection 30 in the front portion thereof acting as a stop, such that it prevents the rotation of the connection portion 17 and its extension 19 in a counter-clockwise direction when the projection 30 of connection portion 17 reaches the end position depicted in FIG. 6a, due to the projection 30 abutting against the inner face 20a of the side wall 20 of the tube 14.

FIGS. 7a and 7b illustrate how the device 1 of FIGS. 6a to 6c adapts to the available intervertebral space 7 between two vertebras 6, which may vary during the service life of the device 1. As shown in FIGS. 7a and 7b, the device 1 advantageously permits the angular position of the connection portion 17 and its extension 19 to vary with respect to the anchoring body 2. The manner in which the active portion 4 of the prosthesis 3 is coupled with the extension 19 also permits a variation in the degree of expansion of the active portion 4 of the prosthesis 3.

Figure 5:
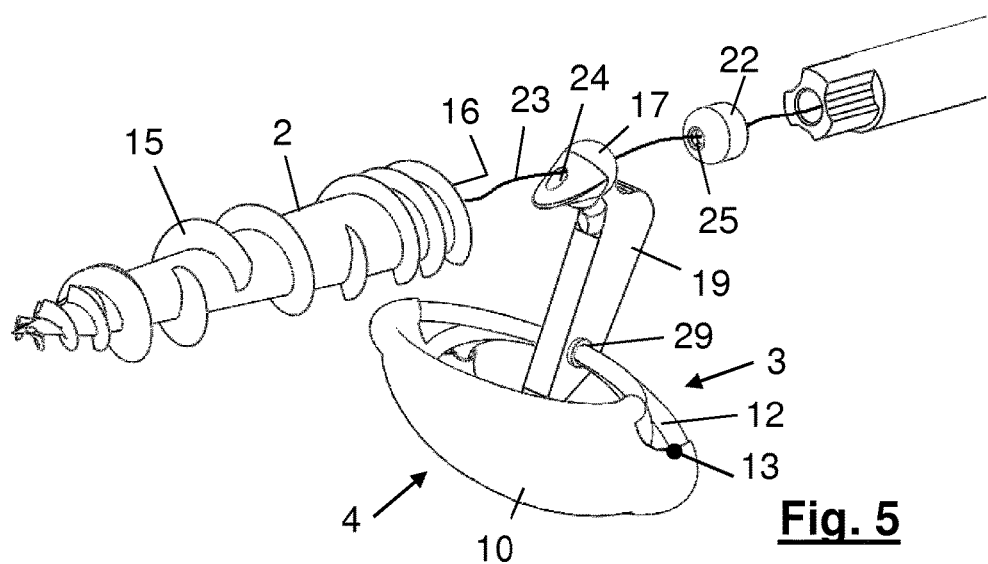
FIG. 5 shows a perspective view of a second variant of the invention.

FIG. 5 illustrates a feature compatible, for example, with both the variant of FIGS. 1 to 2 and with the aforementioned variant of FIGS. 6a to 6c. In the implementation of FIG. 5 a distal end of a thread 23, cable or the like is secured to the anchor body 2 with the thread extending proximally through a tubular portion 14 of the anchoring body 2 and towards the mouth 16. According to some implementations the thread 23 prolongs a sufficient distance so as to be able to emerge from a patient during the implantation of the device 1.

The components of the device 1 intended for being coupled to the anchoring body 2, such as the connection portion 17 and the closure part 22, are provided with respective through holes 24, 25 through which a free end of the thread 23 is inserted so that the thread 23 acts to guide the respective parts relative to one another prior to and during the coupling of the prosthesis 3 to the anchoring body 2. As such, the components 17 and 22, for example, can be slid along the thread 23, leading them to their coupling position for coupling with the anchoring body 2. The thread 23 also acts to prevent the components from inadvertently being lost inside the patient during the positioning and coupling maneuvers with the anchoring body 2. According to some implementations the tool used to position and couple the components to the anchoring body 2 also includes an aperture that receives the free end of the thread 23, as shown in FIG. 5. In such implementations the thread 23 acts to guide the tool into a proper position with the components to be coupled to the anchoring body 2 and also acts to aid in the recovery of the components upon the components being inadvertently dislodged from the tool during the positioning and coupling maneuvers. According to some implementations the thread 23 is made of an absorbable material such as, for example, Vicryl™.

Figure 8A:
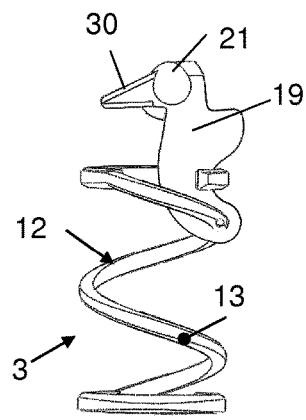
FIGS. 8a to 10 show alternative embodiments of the invention.
Figure 8B:
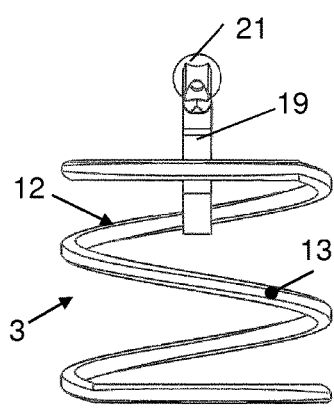
Figure 8C:
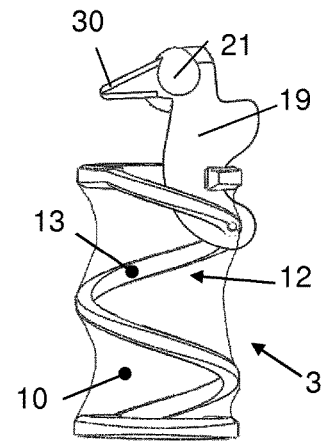

FIGS. 8a, 8b and 8c show an alternative embodiment of the active portion 4 of the prosthesis 3. In this alternative embodiment the frame 12 comprises a spiral-shaped filamentous element 13, shaped like a coil or spring as shown in FIGS. 8a to 8c. The filamentous element 13 is provided with a flexible membrane 10, as shown in FIG. 8c. The flexible membrane 10 can be for example a mesh provided with a channel through which the spiral-shaped filamentous element 13 passes.

Said flexible membrane 10 should be arranged such that when the spiral-shaped filamentous element 13 expands from the compressed position determined by the first compact placement A, the flexible membrane 10 adopts a tubular cylindrical-like configuration. One of the terminal coils forming the spiral-shaped filamentous element 13 embraces the extension 19 of the active portion 4, while the preceding coil traverses said extension 19. This arrangement provides a retention effect once the active portion 4 is placed in the damaged disc and the nucleus pulposus pushes against the flexible membrane 10, enhancing the retention effect of the prosthesis 3.

Similar to the embodiment previously described in FIGS. 6a to 7b, the active portion 4 is also provided with a connection portion 17, arranged to be housed inside the tube of the anchoring body, also allowing the advantageous certain play in the coupling between the prosthesis 3 and the anchoring body 2, so when the prosthesis 3 is housed inside the tube of the anchoring body 2, it is provided with a support surface which slides over the inner face of the side wall of the tube, allowing the controlled play between the connection portion 17 and the anchoring body. The support surface 21 is also configured in the form of a hemispherical cap and comprises a projection 30 in the front portion thereof acting as a stop, such that it prevents the rotation of the connection portion 17 and its extension 19 in a counter-clockwise direction due to the projection 30 abutting against the inner face of the side wall of the tube.

The embodiment of FIGS. 8a, 8b and 8c also adapts to the available intervertebral space analogously to the embodiment previously explained in FIGS. 7a to 7b, advantageously permitting the angular position of the connection portion 17 and its extension 19 to vary with respect to the anchoring body 2.

The spiral-shaped filamentous element 13 can comprise a elliptical helix with the endings of the helix being inscribed in parallel planes, as depicted in FIGS. 8a to 8c.

In order to allow a better compression of the spiral-shaped filamentous element 13, the flexible membrane 10 should be correctly folded, for example inwards or outwards, between the coils of the spiral-shaped filamentous element 13 when the active part of the prosthesis adopts its compact placement shape A. To obtain said folding effect, like an accordion, the flexible membrane 10 could be shrunk once placed in the spiral-shaped filamentous element 13, for example by a thermal treatment through which the flexible membrane 10 will adopt the shape depicted in FIG. 8c.

Figure 9:
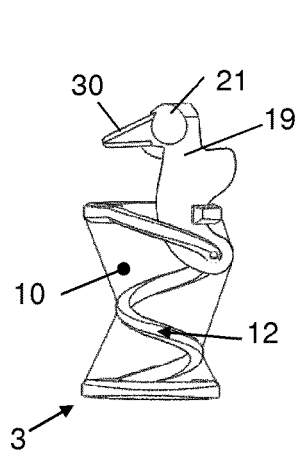
Figure 10:
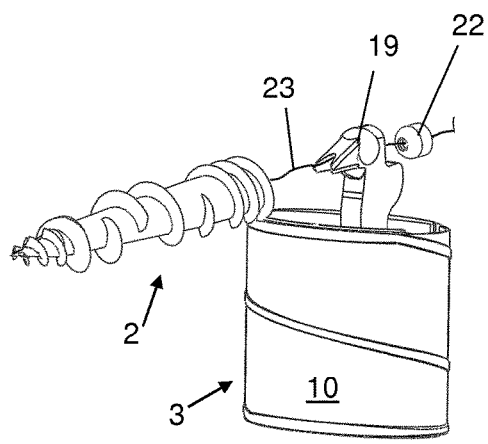

FIG. 9 shows an alternative embodiment of the active portion 4 of the prosthesis 3 that allows a good compression of the spiral-shaped filamentous element 13 by providing a spiral-shaped filamentous element 13 shaped like an elliptical helix with variable pitch, so the different coils of the spiral-shaped filamentous element 13 can be placed within at least one of their adjacent coils in the compact placement shape A FIG. 10 illustrates the arrangement previously described in FIG. 5 but using the active portion 4 of the prosthesis 3 of FIGS. 8a to 8c.

FIGS. 11a and 11b describes the placement of the prosthesis 3 in an intervertebral space 7 in which the anchoring body 2 has been already placed. As can be seen in FIG. 11a, the anchoring body 2 is provided with a thread 23, which acts as a guiding aid for the active portion 4 which would be coupled to the anchoring body 2 while kept in the compact placement shape A, for example when placed within the cannula 35 as depicted in FIG. 11a.

Said thread 23 may also comprise a tubular washer 37 that slides through said thread 23 and that is insertable to the connection portion 17 of the prosthesis 3 and the closure part 22, acting as a rigid guide, once placed within the anchoring body 2, for the prosthesis 3 and the closure part 22.

The thread 23 must also be placed through the connection portion 17 and closure part 22 once the anchoring body 2 is correctly attached to a vertebra, so it can correctly direct said connection portion 17 of the prosthesis 3 and closure part 22 towards the anchoring body 2. In order to allow passing the thread 23 through the connection portion 17 and closure part 22, the thread 23 is advantageously provided with a terminal stiff filamentous part that acts like a needle, allowing the doctor to pass the thread 23 through the connection portion 17 of the prosthesis 3 and closure part 22.

To avoid having to place the prosthesis 3 in the anchoring body 2 and later attaching the closure part 22, the prosthesis 3 and the anchoring body 2 can be engaged for example by means of an auxiliary tip of the tool that would retain the closure part 22, for example an screwdriver, while the closure part 22 is screwed to the anchoring body 2, retaining the prosthesis 3 as shown in FIG. 11b. At this stage, the tubular washer 37 can be cut or removed, together with the thread 23.

Figure 12:
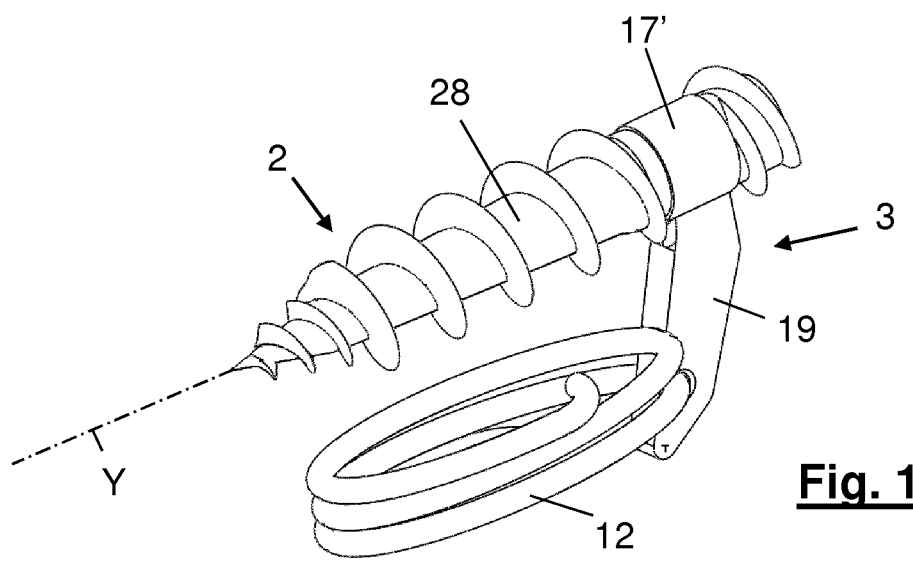
FIGS. 12 and 13 show a fourth variant of the invention.
Figure 13:
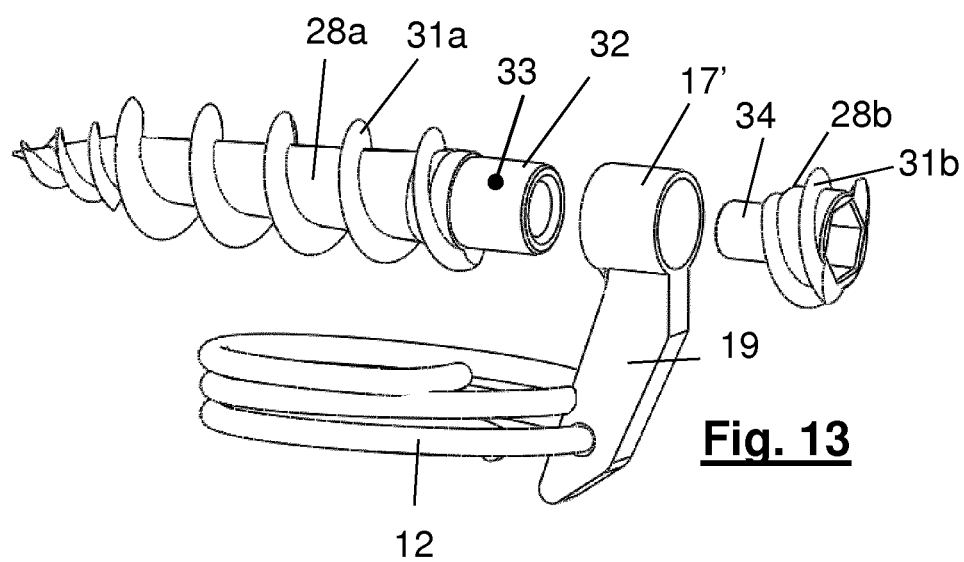

Turning now to FIGS. 12 and 13, another implementation of an intervertebral disc repair device is shown that is particularly suitable for securing the anchoring body 2 to the target vertebra with the prosthesis 3 being previously attached with the anchoring device 2. According to some implementations the anchoring body 2 is configured in the form of a screw 28 extending along a longitudinal axis (Y) and the prosthesis 3 is coupled to the anchoring body 2 with the possibility of rotation about the mentioned longitudinal axis (Y). As shown in FIG. 9, the screw 28 may be split into two parts 28a and 28b both of which are provided with a corresponding outer threading 31a and 31b. The front part 28a comprises a tubular end connecting section 32 for connecting with the rear part 28b, the outer surface 33 of the connecting section 32 being devoid of threads. An annular shaped connection portion 17' of the prosthesis 3 is tightly traversed by the tubular end of the connecting section 32 of the front part 28a of the screw 28 and is assembled on the outer surface 33 thereof, the tightness being selected such that the prosthesis 3 stably maintains a position with respect to the screw 28 by means of friction but allows a rotation of the prosthesis 3 about the screw 28 when a manually applied force is applied thereto. The tubular end of the connecting section 32 may receive therein the coupling of a rod 34 or complementary connecting tube formed for such purpose in the second part 28*b* of the screw 28 so that once the components forming it are suitably coupled, as depicted in FIG. 8, the active portion 4 of the prosthesis, shown in shape (A), may be oriented in the same plane as the longitudinal axis Y of the screw 28. In other implementations the active portion 4 is oriented in a plane not lying along the longitudinal axis Y.

To perform the operation of implanting the anchoring body 2 of FIGS. 12 and 13, and the other implementations disclosed herein, a groove, notch or other type of cavity or opening may be formed in the target vertebra that is intended for receiving at least a portion of the extension 19 that joins the connection portion 17 to the prosthesis 3. The groove, notch or other type of cavity or opening provides a space for receiving at least a portion of the extension 19 as the screw 28 is being secured to the target vertebra, the space having a size and shape suitable for permitting the extension 19 to assume a varying angular orientation with respect to the anchoring body 2 as shown in FIGS. 7*a* and 7*b*. During implantation of the device 1, upon the extension 19 being suitably situated in the groove made in the target vertebra after an initial advancement of the screw 28 into the vertebra, the screw 28 may continue to be advanced to a final anchor position without changing the orientation of the prosthesis 3. As the screw 28 is advanced to the final anchor position the prosthesis 3 is driven forward by the forward movement of the screw 28 until the prosthesis 3 is properly implanted in the nucleus of the disc. Once implanted, the active portion 4 of the prosthesis 3 may be deployed in a manner similar to the implementations described above.

In the foregoing description the prosthesis 3 of the various implementations have comprised active portions 4 suitable for assuming an active expanded shape suitable for effectuating a closure of a damaged portion of an annulus wall/ring of a intervertebral disc upon the prosthesis 3 having been properly implanted within the nucleus of the disc. According to some implementations the active portions 4 have comprised a frame 12 made of one or more filaments 13 arranged to form a plurality of rings that carry with them a membrane 10. It is important to note that the present invention is in no way limited to such prosthetic constructions and that any of a number of other constructions are possible.

In the description that follows intervertebral disc repair devices are disclosed that include prosthesis having one or more buffering elements adapted for being introduced into the nucleus of an intervertebral disc to supplement or replace altogether the functionality of the nucleus pulposus whose function is to absorb forces when the disc is under a compressive load. In instances where only a portion of the nucleus pulposus has escaped or been removed from the disc, a prosthesis comprising the one or more buffering elements may be implanted within the nucleus to supplement the force absorption function of the nucleus pulposus. In instances where all or substantially all of the nucleus pulposus has been removed from the nucleus, the one or more buffering elements may be implanted within the nucleus to replace, at least in part, the force absorption function of the nucleus pulposus.

Figure 16:
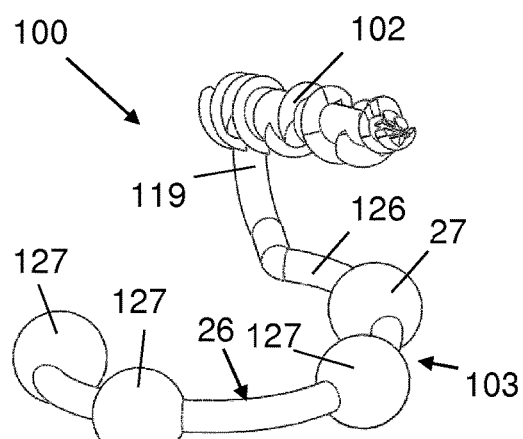
FIGS. 16 to 23 show alternative shapes for respective active portions of a prosthesis of a device according to the invention, spatially suitable for replacing the nucleus pulposus of a damaged human intervertebral disc.

FIG. 16 shows an intervertebral repair device 100 comprising a prosthesis 103 coupled to an anchoring body 102. As with the implementations previously described, the anchoring body 102 comprises a screw 128 adapted to be screwed into the bone mass of a target vertebra for the purpose of anchoring the device 100 thereto. In the implementation of FIG. 12, the prosthesis 103 includes as an active portion a plurality of spaced-apart buffering elements 127 that are interconnected by a core 26 consisting of one or more flexible elements 126, such as one or more flexible wires. Flexible elements other than flexible wires are also contemplated. According to some implementations a proximal end of the wire 126 is coupled with the anchoring body 102 by a rigid or semi-rigid extension 119. The extension 119 may be coupled to the anchoring body 102 by a connector similar to the connectors 17 previously described herein. In other implementations the proximal end 125 of the wire 126 may be coupled to the anchoring body 102 without the use of an extension 119. In such implementations the distal end 125 of the wire may be coupled directly to the anchoring body 102 itself, or alternatively may be coupled to the anchoring body 102 via a connector similar to the connectors 17 previously described herein.

According to some implementations the flexible element 126 comprises a unitary structure or core 26 that is coupled to each of the buffering elements 127. According to some implementations the flexible element 126 passes through a passage provided in each of the buffering elements 127, while in other implementations the flexible element 126 is attached to a surface of each of the buffering elements. In the implementation of FIG. 12, the buffering elements 127 are maintained in a spaced-apart relationship on the flexible element 126. The spaced-apart relationship may be achieved by fixing the buffering elements 127 to the flexible element 126 by use of a glue or other fixing agent. Stops, in the form of radial extending members (not shown) on the flexible wire 126 may also be provided to space the buffering elements from one another. According to some implementations all, or at least some of the buffering elements 127 are free to slide along a length of the flexible element 126. According to some implementations, the flexible element 126 comprises a biocompatible material with elastic and shape memory properties, such as nitinol. The use of a shape memory material advantageously permits the prosthesis 103 to be designed in a manner that results in an active portion or portions of the prosthesis 103 achieving a predetermined form once it has been inserted into the nucleus of the disc. This may, for example, include a predetermined form wherein the prosthesis 103 assumes a spiral configuration within the nucleus. It may also include, for example, a predetermine form wherein the prosthesis 103 assumes a curved shape adapted to the inner lateral wall surfaces of the nucleus. Other predetermined forms are also contemplated, such as a horseshoe arch and circular shapes. The flexible element 126 may also be endowed with the capability of curving over on itself as it is inserted into the space of the nucleus.

The buffering elements 127 may be solid, hollow or can contain in their interior a gel, hydrogel, polymerized liquid, etc. According to some implementations, the buffering elements 127 are made of polyurethane and are intended for tightly fitting between the lower and upper vertebrae of the disc to be repaired. According to other implementations, the buffering elements 127 are inflatable structures. In such implementations the flexible member 126 may comprise a tubular member, such as a hypotube, that is in fluid communication with the interior of the buffering elements 127 and suitable for injecting a gel, hydrogel, polymerized liquid, or the like therein.

Figure 17:
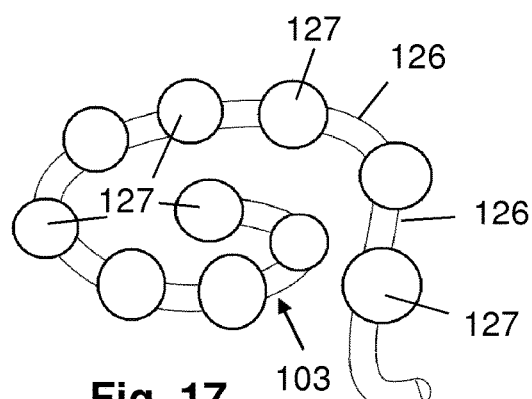

In the implementations of FIGS. 16 and 17, the buffering elements 127 have a spherical configuration, this being a configuration the geometry of which offers good fatigue strength. It can be observed that in the implementations of the FIGS. 12 and 13 that the prosthesis may be outfitted with a varying number of buffering elements 127 and/or buffering elements 127 of varying size. With respect to the latter, as shown in FIGS. 12 and 13, the proximal-most buffering element 127 may be larger than the others being aimed to plug the aperture of the disc through which the prosthesis 103 is inserted. To this end, it is appreciated that the proximal-most buffering element 127 may possess any size and shape suitable for plugging the aperture of the disc. (See, for example, the implementation of FIGS. 10 and 11 which will be discussed in more detail below.) In instances when the cavity of the disc is devoid of the nucleus pulposus, the proximal-most buffering element 127 need not be adapted to plug the aperture, but may instead possess a size and shape adapted at preventing, or at least inhibiting, the prosthesis 103 from passing out of the aperture through which the prosthesis was introduced into the interior space of the disc.

According to other implementations the prosthesis 103 is implanted in the interior of the intervertebral disc without the use of an anchoring body 102. As described above, the prosthesis 103 may be endowed with means of maintaining its position within the interior space of the disc upon its implantation therein. In other implementations the use of staples, stitches, or other fixation means may be used to fix the prosthesis 103 in place upon its implantation within the interior space of the disc.

According to some implementations the flexible element 126 has a diameter in the range of between about 1.0 mm and 3.0 mm and may have a length in the range of between about 40 mm to about 115 mm. According to some implementations the flexibility of element 126 varies along its length. For example, according to some implementations the distal portion of element 126 is more flexible than the proximal portion, the proximal portion being located nearest the anchoring body 102. In such implementations the more flexible distal portion permits the prosthesis 103 to be more readily conformable to the interior space of the disc while the less flexible portion provides a certain degree of rigidity that resists against the prosthesis 103 being forced out of the interior space of the disc when compressive forces are applied to the disc. According to some implementations, the proximal-most segment 128 of the flexible element 126 is endowed with a greater rigidity as compared to the other portions of the flexible element 126 so as to resist buckling. This too resists against the prosthesis 103 being forced out of the interior space of the disc when compressive forces are applied to the disc.

Figure 14:
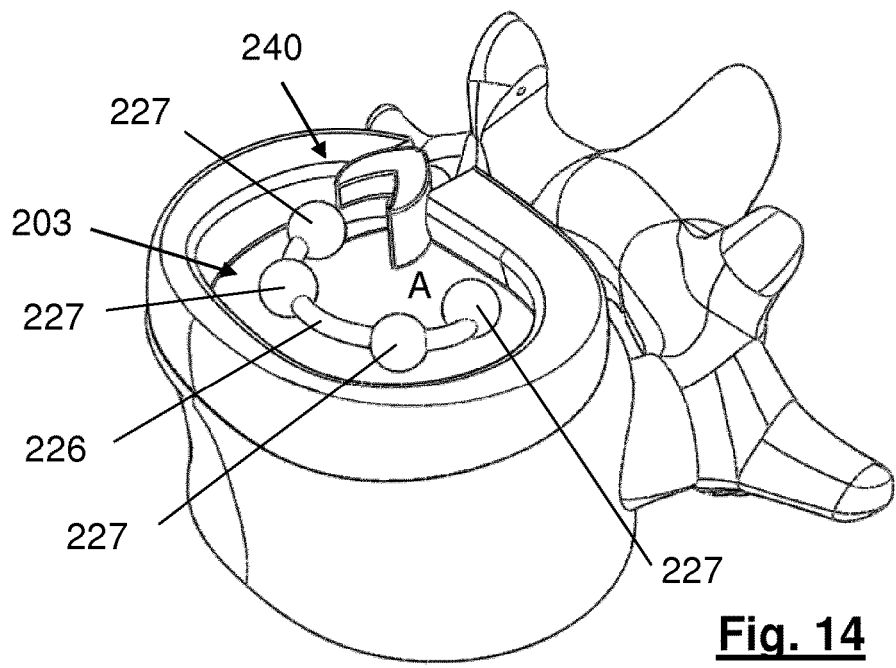
FIGS. 14 and 15 show a fifth variant of the invention.
Figure 15:
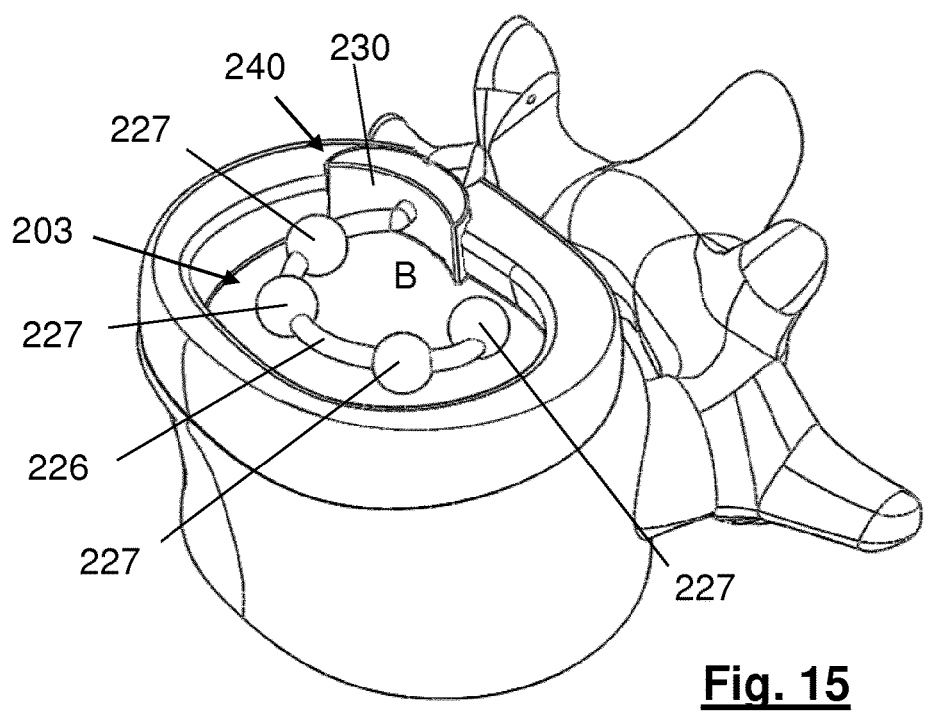

FIGS. 14 and 15 illustrate a portion of an intervertebral disc repair device suitable for replacing part of the nucleus of a damaged intervertebral disc, which may have been subjected to a drainage operation prior to implanting the device. In the example of FIGS. 14 and 15, the prosthesis 203 comprises a plurality of spaced-apart buffering elements 227 disposed on an elongate flexible member 226. A closure member 230 located at a proximal end of the prosthesis is also coupled to the flexible member 226. The closure member 230 is adapted to assume a first compact shape (A) suitable for permitting a delivery of the closure member 230 through the aperture of the disc during implantation of the prosthesis as shown in FIG. 10. Upon the prosthesis being successfully implanted in the interior space of the disc, as shown in FIG. 11, the closure member 230 is adapted to assume a second expanded shape (B). In the implementation shown, a groove 240 in the closure member 230 allows it to assume the first compact state. As previously discussed, the proximal-most element 230 may comprise any size and shape suitable for plugging the aperture in the disc and/or for preventing, or at least inhibiting, the prosthesis from passing out of the aperture through which the prosthesis 203 was introduced into the interior space of the disc. According to some implementations the closure member 230 comprises a polyurethane material and is adapted to assume a crescent shape when it assumes the second expanded shape (B) as shown in FIG. 11. It is appreciated that in such an implementation, as well as others, the closure member 230 may also function as an buffering element. In other implementations the closure member 230 may comprise a frame structure similar to the active portion 4 of the prosthesis 3 described above.

Figure 18:
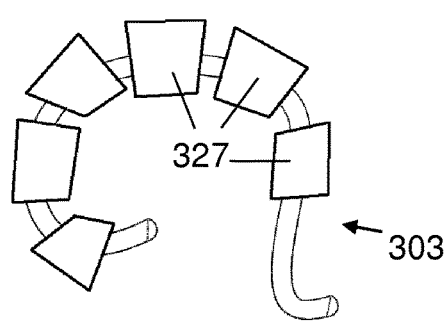
Figure 19:
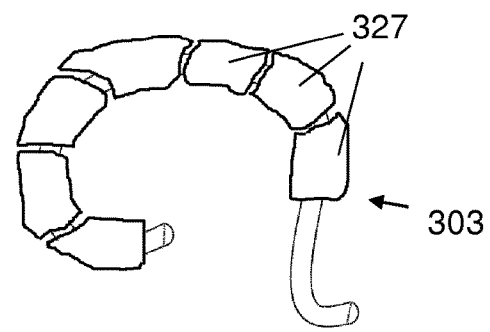

With respect to the implementations of FIGS. 14 through 17, spherical shaped buffering elements have been disclosed. FIGS. 18 and 19 depict implantable prostheses having buffering elements 327 that are in the form cylindrical, polygonal and trapezoidal shapes. An advantage of these shapes is that they offer a larger contact surface between the buffering elements 327 and the vertebrae, favoring the conditions to prevent a collapse of the damaged disc. The prostheses 303 also require less mass from the nucleus to be removed in order to accommodate the insertion of the prostheses into the interior cavity of the disc as compared with prostheses having spherical shaped buffering elements. As discussed above, it is also contemplated that buffering elements 327 may be inflatable, such that they can be introduced in a deflated state making it easier to implant the prostheses 303. With respect to the implementation of FIG. 19, the buffering elements 327 are arranged closer to one another and furthermore have respective complementary adjacent surfaces fitting with one another when the prosthesis adopts a curved shape. This structure offers a larger contact surface between the buffering elements 327 and the vertebrae and additionally facilitates the prosthesis assuming a curved configuration as it is introduced into the intervertebral disc.

Figure 20:
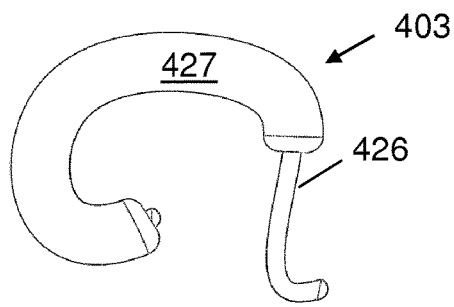
Figure 21:
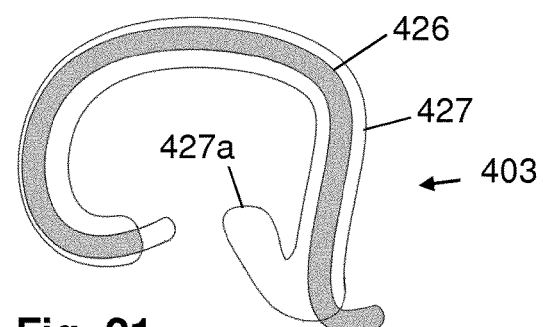

FIGS. 20 and 21 show an alternative in which the prosthesis 403 comprises a single buffering element 427 formed in practice by a covering or case enveloping the elongate flexible element 426 like a sleeve, offering a maximum contact surface with the vertebrae. It is also contemplated that after introducing the buffering element 427 in the interior of the intervertebral disc, the interior of the cover or case can be filled with a filling material such as a gel, a hydrogel, a polymerized liquid, or small particles such as microspheres, to confer strength. The filling materials can be injected into the buffering element 427 once they have been placed in the interior of the intervertebral disc through a cannula or syringe. In the implementations represented in FIGS. 20 and 21, the buffering element 427 has a smooth outer surface. However, in other implementations the outer surface may include an uneven surface in the form of protuberances or other shapes.

FIG. 21 schematically shows a longitudinal section view of a flexible element 426 covered by means of an buffering element 427 in the form of a sleeve which is provided at its proximal end with a fin-like or projection-like extension 427*a* intended for plugging the opening of the disc through which the prosthesis 3 is inserted.

Figure 22:
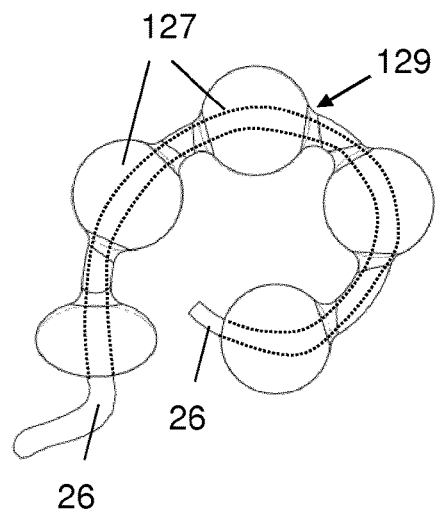

FIG. 22 shows an alternative embodiment in which the core 26 is at least partially covered by several buffering elements 127, and said buffering elements 127 are arranged in a cover 129 of the core 26. Thus, the cover 129 is provided with the buffering elements 127 and the core 26 can be tightly inserted through the cover 129, the cover 129 being arranged to follow the shape that the core 26 adopts. As previously explained, the buffering elements 127 can be elastic or filled with a material such as a gel, a hydrogel, a polymerized liquid, or small particles such as microspheres, to confer strength, and the cover 129 can wrap said buffering elements 127. The buffering elements 127 can be of any shape, for example shaped like the buffering elements depicted in the embodiments of FIGS. 16 to 21. The cover 129 can be made of any flexible material, for example polymeric material. The buffering elements 127 could be the uneven surface in the form of protuberances or other shapes parts of said cover 129, that could be obtained as part of the manufacturing of said cover, for example by filling chambers of said cover 129 or by wrapping elements.

Figure 23:
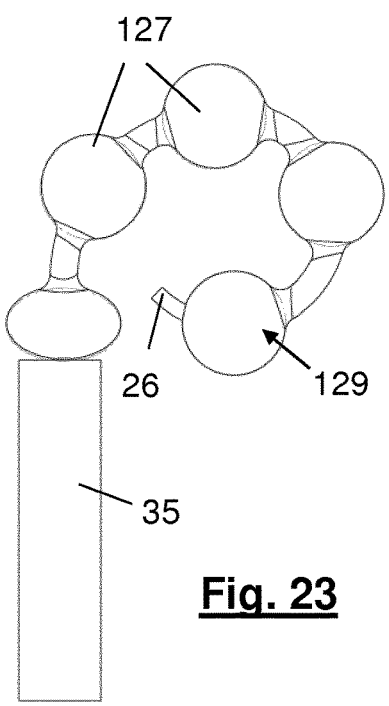

FIG. 23 shows the embodiment depicted in FIG. 22 in which the cover 129 provided with the buffering elements 127 are placed through a cannula 35, for example in the interior of the intervertebral disc. The cannula 35 could be similar to the one previously shown in FIG. 3b, having a longitudinal grove 36 arranged to allow the transit of the extension 19 of the connection portion 17 of the prosthesis 3. The buffering elements 127 of the prosthesis 3 can be compressed when placed within the cannula 35, so when they are released they expand.

Figures 24A, 24B:
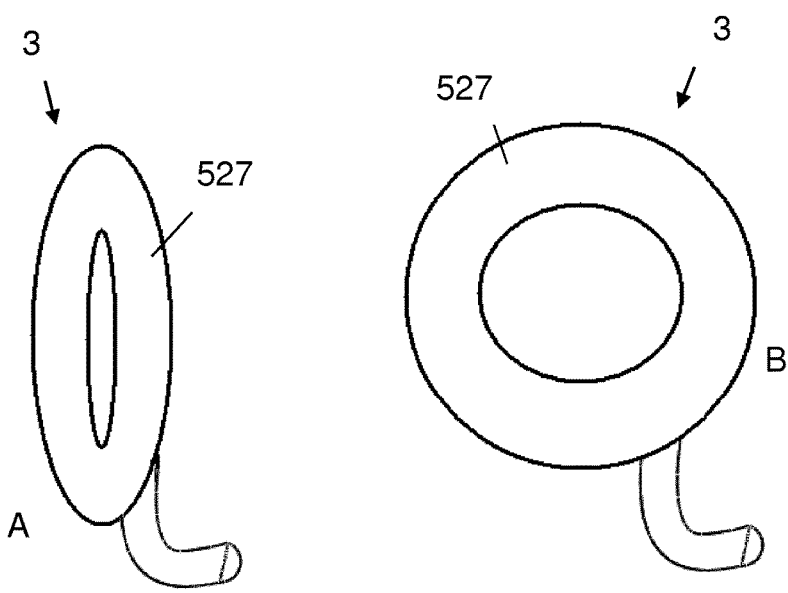
FIGS. 24a and 24b show other forms of realization for an active part of a prosthesis suitable for a device according to the invention.

FIGS. 24a and 24b show other implementations in which the buffering element 527 comprises a substantially toroidal shape. The buffering element 527 may be inserted in the interior of an intervertebral disc as a nucleus prosthesis, replacing the entirety of the nucleus pulposus disc. In a first compact shape (A) the nucleus prosthesis 527 is compressed and essentially straight as shown in FIG. 24a, suitable for being inserted, for example, through a cannula while keeping the first shape (A) during the implantation process. Upon the nucleus prosthesis being fully introduced in the intervertebral space it adopts the second expanded shape (B) as shown in FIG. 24b, filling the space previously occupied by the nucleus pulposus disc.

The nucleus prosthesis can be elastic, made, for example, from a biocompatible flexible material, so that after being deformed and adopting the first compact shape (A), it can automatically return to adopt the second expanded shape (B). The buffering element 527 may be solid, hollow or can contain in its interior a gel, hydrogel, polymerized liquid, etc. According to some implementations, the buffering element 527 is made of polyurethane and is intended for tightly fitting between the lower and upper vertebrae of the disc to be repaired. According to other implementations, the buffering element 527 is an inflatable structure. In such implementations the flexible member 526 may comprise a tubular member, such as a tube, that is in fluid communication with the interior of the buffering elements 527 and suitable for injecting a gel, hydrogel, polymerized liquid, or the like therein. All prosthesis depicted in FIGS. 17 to 24b could be attachable in a secure coupling position to an anchoring body, as shown in FIG. 16, placed in a vertebra, through the procedure explained in the previous embodiments.

The invention claimed is:

1. A device for repairing an intervertebral disc that is disposed between a pair of vertebrae, the device comprising an anchoring body suitable for being advanced into and secured in a vertebrae adjacent the intervertebral disc; and a prosthesis attachable or otherwise attached in a secure coupling position to the anchoring body and adapted for retaining or replacing the nucleus pulposus in an interior space of an outer annulus of the intervertebral disc, the anchoring body configured to support the prosthesis in the coupling position such that the prosthesis may be oriented in a direction toward the outer annulus during an implantation of the prosthesis, the prosthesis comprising at least one active portion configured to assume and maintain a first placement shape suitable for permitting the active portion to be inserted into and through a hole in the outer annulus during a placement thereof into the interior space of the outer annulus, and at least a second operative shape suitable for at least partially occluding the hole in the outer annulus and/or replacing at least a portion of the nucleus pulposus upon the active portion assuming a placement position in the interior space of the outer annulus.

2. The device according to claim 1, wherein the anchoring body comprises an elongated shape and has a first end and a second end, the prosthesis configured to extend from a side of the anchoring body in the coupling position.

3. The device according to claim 2, wherein the active portion of the prosthesis tends to adopt the operative shape by default, the active portion of the prosthesis being provided with one or more retaining elements that forces the active portion to adopt the first placement shape, the one or more retaining elements being manipulable or removable in order to cause the active portion to assume the operative shape.

4. The device according to claim 3, wherein the one or more retaining elements comprise a thread with ties or knots that cooperate in the fastening of the active portion of the prosthesis.

5. The device according to claim 1, wherein the active portion of the prosthesis in the first placement shape resides inside a cannula having an opening at a first end through which the prosthesis may be expelled.

6. The device according to claim 1, wherein the first placement shape is a compact shape and the operative shape is an expanded shape in relation to the first placement shape.

7. The device according to claim 6, wherein the active portion of the prosthesis comprises a flexible membrane supported on a frame, the frame transitional between an unexpanded state and an expanded state and having elastic and shape memory properties that gives the frame the capability to automatically transition from the unexpanded state to the expanded state.

8. The device according to claim 7, wherein the frame comprises one or more spiral-shaped filamentous elements.

9. The device according to claim 8, wherein the one or more spiral-shaped filamentous elements are configured to expand into a fan-like configuration as the frame transitions from the unexpanded state to the expanded state.

10. The device according to claim 8, wherein the one or more spiral-shaped filamentous elements expand to form a tubular-like configuration as the frame transitions from the unexpanded state to the expanded state.

11. The device according to claim 10 wherein the membrane is situated on the frame to also assume a tubular-like configuration when the frame is in the expanded state.

12. The device according to claim 10, wherein the one or more spiral-shaped filamentous element are shaped to form an elliptical helix when the frame is in the expanded shape.

13. The device according to claim 12, wherein the elliptical helix has a variable pitch.

14. The device according to claim 12, wherein the elliptical helix has a first end portion and a second end portion that are arranged substantially parallel to one another.

15. The device according to claim 8, wherein the flexible membrane is arranged on the frame in a manner that causes portions of the flexible membrane located between the windings of the helix to extend inward or outward of the frame as the frame adopts the unexpanded state.

16. The device according to claim 8, wherein the flexible membrane is a mesh provided with a channel through which the one or more spiral-shaped filamentous elements passes.

17. The device according to claim 7, wherein the flexible membrane is heat shrunk onto at least a portion of the frame.

18. The device according to claim 1, wherein the anchoring body extends longitudinally according to an anchoring vector (d1), the prosthesis supported and arranged by the anchoring body when attached in the secure coupling position such that the active portion of the prosthesis is suspended from the anchoring body in a same plane with the anchoring vector (d1).

19. The device according to claim 1, wherein the anchoring body and the prosthesis are configured to be coupled to one another after the anchoring body is secured in one of the vertebrae.

20. The device according to claim 19, wherein the anchoring body comprises a longitudinal portion in the form of a tube defining a mouth through which a connection portion of the prosthesis can be introduced in the anchoring body, the tube being provided with at least one assembly groove so that an extension of the connection portion of the prosthesis, attached to the active portion of the prosthesis, can emerge from the anchoring body through a side wall of the tube.

21. The device according to claim 20, wherein the connection portion of the prosthesis which is configured to be housed inside the tube is provided with a support surface which is adapted to slide over an inner face of the side wall of the tube to allow controlled play between the connection portion and the anchoring body, and thereby of the prosthesis with respect to the anchoring body.

22. The device according to claim 20, further comprising a closure part that can be inserted into the mouth of the tube.

23. The device according to claim 22, wherein the closure part can be screwed into the mouth of the tube.

24. The device according to claim 22, wherein the closure part is reversely attached to the connection portion of the prosthesis.

25. The device according to claim 20, further comprising a thread or cable secured in the tube of the anchoring body, extending through an inner cavity thereof towards the mouth, and prolonging a sufficient distance so as to be able to emerge from a patient during an implantation of the device, the connection portion of the prosthesis being provided with a through hole through which the free end of the thread or cable can be inserted.

26. The device according to claim 25, wherein the thread or cable comprises a terminal stiff filamentous part.

27. The device according to claim 5, further comprising a tubular washer, slidable mounted on the thread or cable and insertable to the connection portion of the prosthesis.

28. The device according to claim 1, wherein the anchoring body is configured in the form of a screw prolonging along a longitudinal axis, the prosthesis attachable or attached to the anchoring body in a manner that permits a rotation of the prosthesis about the longitudinal axis.

29. The device according to claim 1, wherein the placement shape is a substantially straight shape and the operative shape is one of a toroidal, a horseshoe arch or spiral shape the outer contour of which adapts to the space available in the cavity of a damaged human intervertebral disc.

30. The device according to claim 29, wherein the active portion of the prosthesis comprises a core made of a material with elastic and shape memory properties, at least partially covered by at least one buffering element.

31. The device according to claim 30, wherein the core is at least partially covered by a plurality of buffering elements.

32. The device according to claim 30, wherein the at least one buffering element is arranged in a cover of the core.

* * * * *